US005653984A

United States Patent [19]
Fodor et al.

[11] Patent Number: 5,653,984
[45] Date of Patent: Aug. 5, 1997

[54] EXTRACT OF PERIWINKLE SEED AND COMPOSITIONS CONTAINING THE SAME

[75] Inventors: Pierre Fodor, Garches; Gerard Guth, Montmorency; Emmanuelle Maurin, Versailles, all of France

[73] Assignee: L'Oreal, Paris, France

[21] Appl. No.: 499,915

[22] Filed: Jul. 11, 1995

[30] Foreign Application Priority Data

Jul. 11, 1994 [FR] France .................. 94 08566

[51] Int. Cl.$^6$ .......................... A61K 35/78; A61K 38/00
[52] U.S. Cl. .......................... 424/195.1; 514/2; 514/23; 514/557; 514/724
[58] Field of Search ........................... 424/195.1; 514/2, 514/23, 557, 724

[56] References Cited

U.S. PATENT DOCUMENTS 4,952,392  8/1990  Thame ................................ 424/58

OTHER PUBLICATIONS

Garg et al., *The Journal of the Oil Technologists' Association of India*, vol. 19, pp. 63–64 (1987).

*Primary Examiner*—John W. Rollins
*Attorney, Agent, or Firm*—Oblon, Spivak, McClelland, Maier & Neustadt, P.C.

[57] ABSTRACT

Extracts of periwinkle seed, obtained by bioconversion, and compositions containing such extracts display the property of stimulating mitochondrial cell respiration and of stimulating the cell growth of fibroblasts and keratinocytes. Such extracts and compositions also exhibit activity against oxygen free radicals.

27 Claims, No Drawings

EXTRACT OF PERIWINKLE SEED AND COMPOSITIONS CONTAINING THE SAME

BACKGROUND OF THE INVENTION

1. Field of the Invention

The present invention relates to extracts of periwinkle seed and to their use for stimulating cell respiration, and also cell growth, and for protecting against free radicals, in particular in the cosmetic and/or dermatological fields. More especially, such extracts may be used in compositions intended for preventing and/or combatting skin ageing and/or for protecting the skin, hair, and/or mucosae.

2. Discussion of the Background

In the cosmetic and dermatological fields, much effort is expended in the search for agents which will stimulate cell respiration and cell growth and which will protect cells against the effects of free radicals. Such agents are desired for use in compositions for preventing and/or combatting the ageing of skin and/or for protecting the skin, hair, and/or mucosae. However, to date, no completely satisfactory agents or compositions are known.

The periwinkle is a plant found in shady places, having blue flowers with spreading lobes and shiny leaves. Two major families of periwinkle are distinguished, the American periwinkle or *Vinca rosea*, and the tropical periwinkle or *Catharanthus roseus*. Periwinkle leaves and stems are known to contain alkaloids which have advantageous pharmacological properties. As a result, periwinkles are used, for example, in antidiarrheal and antihaemorrhagic preparations, and for preventing the onset of lactation. Alkaloids isolated from the American periwinkle are used, in particular, for the treatment of Hodgkin's disease or of certain malignant tumors.

However, periwinkle seeds have never been subjected hitherto to research with a view to determining particular properties.

Thus, there remains a need for agents and compositions which are effective for stimulating cell respiration and cell growth and protecting cells from the effects of free radicals. There also remains a need for agents and compositions useful for preventing and/or combatting the ageing of skin and/or for protecting the skin, hair, and/or mucosae.

SUMMARY OF THE INVENTION

Accordingly, it is one object of the present invention to provide novel agents useful for stimulating cell respiration and cell growth and protecting cells against the effects of free radicals.

It is another object of the present invention to provide novel agents useful for preventing and/or combatting the ageing of skin and/or for protecting skin, hair, and/or mucosae.

It is another object of the present invention to provide a novel method for preparing such an agent.

It is another object of the present invention to provide novel compositions which contain such an agent.

These and other objects, which will become apparent during the following detailed description, have been achieved by the inventors' discovery that an extract can be obtained from periwinkle seeds which displays highly advantageous properties, in particular in the cosmetic and dermatological fields. In the context of the present application, the term "extract" is understood to mean a substance extracted by a physical, chemical and/or biotechnological operation.

In addition, the inventors have found that, contrary to the stems and leaves, the seed extract does not contain any alkaloid.

Thus, one aspect of the present invention is an extract isolated from periwinkle seed containing proteins, amino acids, organic acids and nutrient ingredients, this extract being obtained, in particular, by bioconversion.

The present extract contains, in particular, proteins, amino acids (glutamic acid, proline, lysine, valine, leucine, aspartic acid and most especially methionine), organic acids (lactic acid) and sugars (lactose).

According to a preferred embodiment of the present invention, tropical periwinkle seeds, and more especially the Madagascar periwinkle seed, are used to obtain the present extract.

According to the present invention, the extract is obtained by bioconversion of ground periwinkle seeds.

Thus, another aspect of the present invention is a process for obtaining an extract of periwinkle seed, characterized in that the process comprises grinding the periwinkle seeds, subjecting the ground seeds to an enzyme predigestion in the presence of amylase and/or cellulase and then to a fermentation in the presence of microorganisms, and then filtering the fermentation culture.

According to a preferred embodiment of the present invention, the microorganisms used for the fermentation are lactic microorganisms known as lactobacilli.

A further aspect of the present invention is a composition comprising an extract of periwinkle seed.

Another aspect of the present invention is a composition comprising an extract of periwinkle seed obtained by the process defined above.

According to a preferred embodiment, the composition according to the present invention comprises a cosmetically and/or dermatologically acceptable medium.

The inventors have found, unexpectedly, that the extract according to the present invention displays the property of stimulating mitochondrial cell respiration and the cell growth of fibroblasts and keratinocytes. Furthermore, the present extract has a protective activity against free radicals, in particular oxygen free radicals. In the context of the present invention, the term "oxygen free radicals" is understood to mean all reactive species of non-molecular oxygen, and in particular singlet oxygen.

Thus, the present invention also provides a composition for stimulating cell respiration and/or cell growth and/or preventing free-radical formation, characterized in that it comprises an extract as defined above.

The present invention also provides a composition for preventing and/or combatting skin ageing and/or for protecting and/or nourishing the skin, hair and/or mucosae, in particular against the harmful and/or unsightly effects caused by free radicals, characterized in that it comprises an extract as defined above.

An additional aspect of the present invention is the use of the present extract of periwinkle seed as defined above in a cosmetic and/or dermatological composition intended for stimulating cell respiration and/or cell growth and/or for preventing free-radical formation.

Another aspect of the present invention is the use of the extract of periwinkle seed as defined above in a cosmetic and/or dermatological composition intended for preventing and/or combatting skin ageing and/or for protecting and/or nourishing the skin, hair and/or mucosae, in particular against the harmful and/or unsightly effects caused by free radicals.

An additional aspect of the present invention is a process for preventing and/or combatting skin ageing and/or protecting and/or nourishing the skin, hair and/or mucosae, characterized in that a composition as defined above is applied to the skin, hair and/or mucosae.

DETAILED DESCRIPTION OF THE PREFERRED EMBODIMENTS

The present extract of periwinkle seed may be prepared by a process comprising:

(a) grinding periwinkle seed, to obtain ground periwinkle seed;

(b) subjecting the ground periwinkle seed to enzyme predigestion with an amylase and/or cellulase, to obtain predigested periwinkle seed;

(c) subjecting the predigested periwinkle seed to fermentation in the presence of a microorganism, to obtain fermented periwinkle seed; and (d) filtering said fermented periwinkle seed, to obtain said extract.

As noted above, the periwinkle seed used to prepare the present extract is preferably tropical periwinkle seed, more preferably Madagascar periwinkle seed. The periwinkle seed may be ground with any suitable apparatus, such as a mortar and pestel, a blender, a mill, etc. The exact size that the periwinkle seed is ground to is not critical so long as the shell of the seed is broken to expose the inside of the seed. Typically, the periwinkle seed will be ground to a size of 0.1 to 1 mm.

The predigestion of the ground periwinkle seed is carried out by contacting the ground periwinkle seed with an amylase and/or cellulase. Suitable amylases include Type I-A: DFP treated from procine pancreas; Type I-A: PMSF treated from porcine pancreas; Type II-A: from Bacillus sp.; Type VI-B: from porcine pancreas; Type III-A: DFP treated from porcine pancreas; Type VIII-A: from barley malt; Type IX-A: from human saliva; Type X-A: from *Aspergillus oryzae*; Type XII-A: from *Bacillus licheniformis*; Type XIII-A: from human saliva; and the same amylases immobilized on beaded agarose or polyacrylamide. Suitable cellulases include irradiated and nonirradiated cellulase from *Aspergillus niger*, cellulase from *Trichoderma reesei*; cellulase from *Trichoderma viride*; and cellulase from *Penicillium funiculosum*. Such amylases and cellulases are commercially available from Sigma Chemical Co., St. Louis, Mo.

The predigestion may be carried out by contacting the ground periwinkle seed with the amylase and/or cellulase in an aqueous solution. The aqueous solution may also contain a buffer to maintain the pH in the range of from 4 to 6. Typically, the predigestion is carried out at a temperature of 20° to 40° C., preferably 25° to 35° C., for a time of 2 to 5 days, preferably 2 to 3 days. The predigestion may be carried out in any suitable apparatus such as a Biolafitte type fermentor. Typically, the predigestion is performed using 1 to 2% of amylase and/or cellulase per gram of ground periwinkle seed.

After the predigestion of the periwinkle seed is complete, the predigested periwinkle seed is then subjected to a fermentation in the presence of a microorganism. As noted above, the fermentation is preferably carried out in the presence of lactic microorganisms known as lactobacilli.

The fermentation is usually carried out in a culture medium which contains peptones and optionally yeast extract. Such media are commercially available from Bio-Merieux or Merck. The fermentation is typically carried out at a temperature of from 34° to 40° C., preferably about 37° C., for a time of 4 to 10 days, preferably about 1 week. The pH of the fermentation culture is suitably maintained at a value of 4 to 7, preferably 5 to 6. The amount of predigested periwinkle seed is suitably 1 to 10% by weight, preferably 1 to 5% by weight, based on the total weight of the fermentation medium.

The fermentation is carried out under aerobic conditions, and the fermentation medium is inoculated with the microorganism in the form of a preculture medium. The conditions of the preculture are the following: the bacteria (lactobacilli) are invigorated in a liquid nutrient medium, then subcultured twice and inoculated in a culture medium. The initial pH is 5.5. The growth lasts for 72 hours and the latent period is 20 hours. Then, there is inoculation of the fermenter at 15 liters in the same conditions, and then inoculation of the production of 600–800 liters. The liquid nutrient medium used in the preculture has the following composition:

| Peptone | 10–20 g/l |
|---|---|
| Yeast Extract | 3–10 g/l |
| Sodium acetate | 5 g/l |
| Di-ammonium citrate | 2 g/l |
| Dipostassium phosphate | 2–3 g/l |
| Tween 80 (Polysorbate 80) | 1–2 g/l |
| $MgSO_4.7H_2O$ | 0.1–0.5 g/l |
| $MnSO_4.4H_2O$ | 0.02–0.05 g/l |
| Glucose | 10–20 g/l |

After the fermentation is complete, the fermentation medium is then filtered to remove particulates and the microorganisms and to obtain the extract as the filtrate. Any suitable filtering device capable of removing the particulate matter and microorganisms may be used, such as a glass frit with a pore size of 0.30 to 500 µm, preferably 0.45 to 400 µm.

Typically, the present extract of periwinkle seed will comprise 70 to 85% by weight of water, 8 to 16% by weight of a polyol (glycerin), 2 to 6% by weight of proteins and amino acids, 0.5 to 1.5% of lactic acid, and 0.01 to 0.2% of lactose.

The extract of periwinkle seed according to the present invention can, for example, be used in a cosmetic and/or dermatological composition at a concentration ranging from 0.05% to 15% by weight, preferably from 0.1% to 10% by weight, more preferably from 0.5 to 10% by weight, based on the total weight of the composition.

The compositions according to the present invention may be presented in all dosage forms normally used for topical application or administration by injection or by oral administration, intended especially for the cosmetic and/or dermatological fields. In particular, the present compositions can take the form of aqueous, alcoholic, or aqueous-alcoholic solutions, the form of creams, hydrophilic or lipophilic gels, water-in-oil or oil-in-water emulsions, creams or gels capable of foaming, compositions in aerosol form or alternatively in the form of microgranules, powders or vesicular dispersions of the ionic and/or nonionic type. These compositions are prepared according to the standard methods of the fields in question.

The amounts of the different constituents of the compositions according to the invention are those traditionally used in the cosmetic or pharmaceutical fields or the field of hygiene.

The present compositions include, in particular, face, neck, hand or body cleansing, protection, treatment or care compositions (for example day creams, night creams, make-up-removal creams, sun creams or oils, cleansing milks, make-up-removal milks, body milks), make-up compositions (for example make-up foundations), artificial tanning compositions or bath compositions.

The compositions according to the present invention can also be in the form of solid preparations including cleansing soaps or bars.

The present extracts may also be used in various compositions for the hair, and in particular shampoos, setting lotions, treatment lotions, styling creams or gels, dyeing compositions, and lotions or gels for combatting hair loss.

The cosmetic compositions of the present invention can also have a anticatarrhal application and can, for example, take the form of a toothpaste.

When the composition of the present invention is an emulsion, the proportion of fats can range from 5% to 80% by weight, and preferably from 5% to 50% by weight, based on the total weight of the composition. The fats and the emulsifiers used in the composition in emulsion form are chosen from those traditionally used in the cosmetic field. The emulsifiers can be present in the composition in a proportion ranging from 0.3% to 30% by weight, preferably from 0.5 to 30% by weight, based on the total weight of the composition. The emulsion can, in addition, contain lipid vesicles.

The cosmetic composition of the present invention can, in a conventional manner, also contain adjuvants which are customary in the cosmetic field, such as hydrophilic or lipophilic gelling agents, hydrophilic or lipophilic active agents, preservatives, antioxidants, solvents (alcohols), perfumes, fillers, sunscreen agents and colorants. The amounts of these different adjuvants are those conventionally used in the cosmetic field, and are, for example, from 0.01% to 10% of the total weight of the composition. These adjuvants, depending on their nature, may be introduced in the fatty phase, in the aqueous phase and/or in the lipid spherules.

As fats which may be used in the present compositions, there may be mentioned mineral oils, vegetable oils (for example liquid fraction of shea butter, apricot-kernel oil, mango-kernel oil) and their hydrogenated derivatives (for example hydrogenated palm oil), animal oils, synthetic oils (for example capric/caprylic triglycerides), silicone oils (for example cyclomethicones and dimethicones) and fluorinated oils. Other fats such as fatty alcohols (for example cetyl alcohol), fatty acids (for example stearic acid) and waxes (for example vegetable wax) may be added to these oils.

As emulsifiers which may be used in the present compositions, the cetearyl glucoside sold under the name Montanov 68 by the company Seppic, or the mixture of sucrose cocoate and sorbitan stearate sold under the name Arlatone 2121 by the company ICI, may be mentioned by way of example.

As hydrophilic gelling agents which may be used in the present compositions, there may be mentioned, for example, carboxyvinyl polymers (carbomer), acrylic copolymers such as acrylate/alkyl acrylate copolymers, polyacrylamides, polysaccharides such as hydroxyethylcellulose, natural gums (for example xanthan gum, sclerotium gum) and clays, and as lipophilic gelling agents, there may be mentioned modified clays such as bentones, metal salts of fatty acids such as aluminum stearates, and hydrophobic silica.

Hydrophilic active agents which may be used in the present compositions include proteins or protein hydrolysates, amino acids, polyols, urea, allantoin, sugars and sugar derivatives, vitamins, and hydroxy acids.

Lipophilic active agents which may be used in the present compositions include retinol (vitamin A) and its derivatives, tocopherol (vitamin E) and its derivatives such as vitamin E acetate, essential fatty acids, ceramides, essential oils, and salicylic acid and its derivatives.

Other features of the invention will become apparent in the course of the following descriptions of exemplary embodiments which are given for illustration of the invention and are not intended to be limiting thereof.

EXAMPLES

In the following examples, all amounts shown are % by weight, unless otherwise indicted. The term "qs 100%" means that ingredient is present in an amount sufficient to make the total amount of all ingredients equal 100% by weight.

Example 1

Example of Preparation of the Extract of Periwinkle Seed

*Catharanthus roseus*, periwinkle seeds are ground in a mortar. The ground preparation obtained is subjected to an enzyme predigestion with an amylase and a cellulase in a Biolafitte type fermenter, and then to a fermentation in the presence of lactic microorganisms, this fermentation being carried out for 1 week. The nutrient medium for the fermentation contains, in particular, peptones with or without the addition of yeast extract, and is sold by Bio-Mérieux or Merck. It is maintained at a temperature of 37° C. and at a pH adjusted to between 5 and 6. The fermentation medium is then filtered under a controlled atmosphere in order to remove the ground preparation residues and the microorganisms from it. The obtained extract is in an aqueous medium.

This extract contains 78.2% of water, 12.8% of a polyol (glycerin), 4.6% of proteins and amino acids, 1% of lactic acid, 0.08% of lactose.

This extract has the following centesimal composition in amino acids after hydrolysis:

aspartic acid: 5.8%;

threonine: 4.2%;

serine: 5.5%;

glutamic acid: 22.5%;

proline: 10%;

glycine: 2.3%;

alanine: 3.7%;

valine: 6.8%;

cystine: 0.3%;

methionine: 2.5%;

isoleucine: 5.4%;

leucine: 9.6%;

tyrosine: 2.3%;

phenylalanine: 4.6%;

lysine: 8.5%;

arginine: 3.3%; and ornithine: 0.2%.

This hydrolysis was performed in an autocatalysor (Hitachi L8500) with 9N HCl over 4 hours at 120° C.

Example 2

Skin Care Cream

Oily phase:

| | |
|---|---|
| Cetearyl glucoside (sold under the name Montanov 68 by the company Seppic) | 2.0% |
| Cetyl alcohol | 1.5% |
| Vegetable wax (sold under the name Suma Wax by the company Noda) | 2.0% |
| Liquid fraction of shea butter | 3.0% |
| Apricot-kernel oil | 12.0% |
| Mango-kernel oil | 2.0% |
| Dimethicone (sold under the name Silicone L-45 by the company Union Carbide) | 1.0% |

Aqueous phase:

| | |
|---|---|
| Glycerol | 3.0% |
| Hydroxyethylcellulose (gelling agent) | 0.2% |
| Sclerotium Gum (sold under the name Amigel by the company Alban Muller) (gelling agent) | 0.5% |
| Starch (filler) | 0.4% |
| Extract of periwinkle seed obtained in Example 1 | 2.5% |
| Preservatives | qs |
| Perfume | 0.2% |
| Water | qs 100% |

The method of preparation of the emulsion consists of mixing the oily phase in the aqueous phase at a temperature of approximately 70° C. to 80° C. while stirring using a turbo-mixer.

The product obtained is an oil-in-water emulsion which has the appearance of a cream and may be used as a night cream to be applied daily.

Example 3

Mask

Oily phase:

| | |
|---|---|
| Octyldodecanol (emollient) | 6.0% |
| Apricot-kernel oil | 6.0% |
| Capric/caprylic triglycerides | 5.0% |
| Kaolin (filler) | 3.0% |
| Cetyl alcohol | 2.0% |
| Vitamin E acetate | 0.5% |
| Hydrogenated palm oil | 6.0% |
| Liquid fraction of shea butter | 5.0% |

Aqueous phase:

| | |
|---|---|
| Xanthan gum (gelling agent) | 0.4% |
| Sucrose cocoate/sorbitan stearate (mixture sold under the name Arlatone 2121 by the company ICI) (emulsifier) | 5.5% |
| Glycerol | 3.0% |
| Extract of periwinkle seed obtained in Example 1 | 3.0% |
| Perfume | 0.3% |
| Preservatives | qs |
| Water | qs 100% |

The method of preparation of the emulsion is the same as in Example 2.

The product obtained is an oil-in-water emulsion which has the appearance of a cream. It is used in the customary manner for masks, that is to say it is applied to the face and, after a certain exposure time, namely approximately 3 to 10 min, it is rinsed off with water.

This application is based on French Patent Application 94-08566 filed on Jul. 11, 1994, which is incorporated herein by reference.

Obviously, numerous modification and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. An extract isolated from periwinkle seed, said extract comprising proteins, amino acids, organic acids and sugars, and being obtained by bioconversion.

2. The extract of claim 1, further comprising a polyol.

3. The extract of claim 2, wherein said organic acids comprise a carboxylic acid and said sugars comprise lactose, and comprising 12.8% by weight of said polyol, 4.6% by weight of said proteins and amino acids, 1% by weight of said carboxylic acid, and 0.8% by weight of lactose, based on the total weight of said extract.

4. The extract of claim 1, wherein said amino acids comprise aspartic acid, threonine, serine, glutamic acid, proline, glycine, alanine, valine, cystine, methionine, isoleucine, leucine, tyrosine, phenylalanine, and lysine.

5. The extract of claim 1, wherein, after hydrolysis, amino acids are present in a percent amount of:

aspartic acid: 5.8%;

threonine: 4.2%;

serine: 5.5%;

glutamic acid: 22.5%;

proline: 10%;

glycine: 2.3%;

alanine: 3.7%;

valine: 6.8%;

cystine: 0.3%;

methionine: 2.5%;

isoleucine: 5.4%;

leucine: 9.6%;

tyrosine: 2.3%;

phenylalanine: 4.6%;

lysine: 8.5%;

arginine: 3.3%; and ornithine: 0.2%.

6. The extract of claim 1, wherein said organic acids comprise lactic acid.

7. The extract of claim 1, wherein said sugars comprise lactose.

8. A process for obtaining an extract of periwinkle seed, comprising:

(a) grinding periwinkle seed to obtain ground periwinkle seed;

(b) subjecting said ground periwinkle seed to enzyme predigestion with an amylase, a cellulase or a mixture thereof to obtain predigested periwinkle seed;

(c) subjecting said predigested periwinkle seed to fermentation in the presence of a microorganism to obtain fermented periwinkle seed; and (d) filtering said fermented periwinkle seed to obtain said extract.

9. The process of claim 8, wherein said periwinkle seed is tropical periwinkle seed.

10. The process of claim 8, wherein said fermentation is carried out in the presence of a lactic microorganism.

11. The process of claim 8, wherein said fermentation is carried out for one week.

12. A composition comprising an extract of periwinkle seed, said extract comprising proteins, amino acids, organic acids and sugars, and being obtained by bioconversion.

13. The composition of claim 12, wherein said extract of periwinkle seed further comprises a polyol.

14. The composition of claim 13, wherein said organic acids comprise a carboxylic acid and said sugars comprise lactose, and said extract of periwinkle seed comprises 12.8% by weight of said polyol, 4.6% by weight of said proteins and amino acids, 1% by weight of said carboxylic acid, and 0.8% by weight of lactose, based on the total weight of said extract.

15. The composition of claim 12, wherein said amino acids comprise aspartic acid, threonine, serine, glutamic acid, proline, glycine, alanine, valine, cystine, methionine, isoleucine, leucine, tyrosine, phenylalanine and lysine.

16. The composition of claim 12, wherein amino acids are present in said extract, after hydrolysis of said extract, in a percent amount of:

aspartic acid: 5.8%;

threonine: 4.2%;

serine: 5.5%;

glutamic acid: 22.5%;

proline: 10%;

glycine: 2.3%;

alanine: 3.7%;

valine: 6.8%;

cystine: 0.3%;

methionine: 2.5%;

isoleucine: 5.4%;

leucine: 9.6% tyrosine: 2.3%;

phenylalanine: 4.6%;

lysine: 8.5%;

arginine: 3.3%; and ornithine: 0.2%.

17. The composition of claim 12, wherein said organic acid is lactic acid.

18. The composition of claim 12, wherein said sugars comprise lactose.

19. The composition of claim 12, further comprising a cosmetically or dermatologically acceptable medium.

20. The composition of claim 12, wherein said extract is present in an amount of from 0.05% to 15% by weight, based on the total weight of said composition.

21. A composition comprising an extract of periwinkle seed obtained by a process comprising:

(a) grinding periwinkle seed to obtain ground periwinkle seed;

(b) subjecting said ground periwinkle seed to enzyme predigestion with an amylase, a cellulase or a mixture thereof to obtain predigested periwinkle seed;

(c) subjecting said predigested periwinkle seed to fermentation in the presence of a microorganism to obtain fermented periwinkle seed; and (d) filtering said fermented periwinkle seed to obtain said extract.

22. A method of stimulating cell respiration, cell growth or preventing free-radical formation, comprising administering to a subject a composition comprising an effective amount of an extract of periwinkle seed.

23. The method of claim 22, wherein said composition is applied to the skin, hair, or mucosae.

24. The method of claim 22, wherein said effective amount of an extract of periwinkle seed is 0.05% to 15% by weight, based on the total weight of said composition.

25. A method of preventing or combating aging protecting or nourishing the skin, hair or mucosae, comprising administering to a subject a composition comprising an effective amount of an extract of periwinkle seed.

26. The method of claim 25, wherein said composition is applied to the skin, hair, or mucosae.

27. The method of claim 25, wherein said effective amount of an extract of periwinkle seed is 0.05% to 15% by weight, based on the total weight of said composition.

* * * * *